US012605194B2

(12) United States Patent
Bousquet et al.

(10) Patent No.: US 12,605,194 B2
(45) Date of Patent: Apr. 21, 2026

(54) OSTEOSYNTHESIS SCREW WITH ANGULAR INDEXING RELATIVE TO THE SCREWDRIVER AND UNIVERSAL COMPATIBILITY

(71) Applicant: NOVASTEP, Rennes (FR)

(72) Inventors: Adrien Bousquet, La Meziere (FR); Loïc Girod, Goven (FR); Rémi Le Besque, Bruz (FR)

(73) Assignee: NOVASTEP, Rennes (FR)

( * ) Notice: Subject to any disclaimer, the term of this patent is extended or adjusted under 35 U.S.C. 154(b) by 225 days.

(21) Appl. No.: 18/275,078

(22) PCT Filed: Jan. 31, 2022

(86) PCT No.: PCT/FR2022/050168
§ 371 (c)(1),
(2) Date: Jul. 31, 2023

(87) PCT Pub. No.: WO2022/162326
PCT Pub. Date: Aug. 4, 2022

(65) Prior Publication Data
US 2024/0130767 A1 Apr. 25, 2024
US 2024/0225706 A9 Jul. 11, 2024

(30) Foreign Application Priority Data
Feb. 1, 2021 (FR) ...................................... 21/00926

(51) Int. Cl.
*A61B 17/86* (2006.01)
*A61B 17/88* (2006.01)
*B25B 23/10* (2006.01)

(52) U.S. Cl.
CPC ........ *A61B 17/8615* (2013.01); *A61B 17/863* (2013.01); *A61B 17/888* (2013.01); *A61B 17/8888* (2013.01); *B25B 23/108* (2013.01)

(58) Field of Classification Search
CPC .................................................. A61B 17/8615
See application file for complete search history.

(56) References Cited

U.S. PATENT DOCUMENTS 6,953,463 B2 10/2005 West, Jr.
8,257,398 B2 9/2012 Jackson
(Continued)

FOREIGN PATENT DOCUMENTS

EP 1302180 A2 4/2003
EP 2740425 B1 9/2015
(Continued)

OTHER PUBLICATIONS

International Search Report dated May 17, 2022; International Application No. PCT/FR2022/050168; 2 pages (English).
(Continued)

*Primary Examiner* — Olivia C Chang
(74) *Attorney, Agent, or Firm* — Eversheds Sutherland (US) LLP

(57) ABSTRACT

The present invention relates to a clamping screw (6) for osteosynthesis, comprising at least one screw thread (7, 10) along a main axis (X) and, at its end referred to as the apex end (11), having a socket (12) which, about said main axis (A), has evenly angularly distributed shapes designed to accept complementing shapes of a screwdriver (19) engaged in said socket (12), notable in that the socket (12) of the screw (6) comprises at least three regular shapes (13) of which the vertices are inscribed inside a circle referred to as circumscribed circle (30) and at least two adjacent vertices of the socket (21) are connected to form a convex lobe referred to as indexing lobe (16) of which the radius of curvature is equal to the radius of the circumscribed circle (30).

9 Claims, 7 Drawing Sheets

(56) References Cited

U.S. PATENT DOCUMENTS

| | | | |
|---|---|---|---|
| 9,226,775 B2 | 1/2016 | Gorhan et al. | |
| 9,358,057 B1 | 6/2016 | Whipple et al. | |
| 9,867,639 B2 | 1/2018 | Biedermann et al. | |
| 10,070,896 B2 | 9/2018 | Biedermann et al. | |
| 10,499,969 B2 | 12/2019 | Mcgirt | |
| 11,045,239 B2 | 6/2021 | Blitz | |
| 2001/0041937 A1 | 11/2001 | Rieser et al. | |
| 2009/0163961 A1 | 6/2009 | Kirschman | |
| 2010/0211114 A1 | 8/2010 | Jackson | |
| 2016/0038205 A1* | 2/2016 | Smith | A61B 17/1655 606/279 |
| 2020/0085477 A1* | 3/2020 | Blitz | A61B 17/8625 |
| 2020/0229853 A1 | 7/2020 | Girod et al. | |

FOREIGN PATENT DOCUMENTS

| | | | |
|---|---|---|---|
| EP | 2990666 A1 | 3/2016 | |
| FR | 2760628 A1 | 9/1998 | |
| FR | 2808182 A1 | 11/2001 | |
| MX | 2016006587 A | 8/2016 | |
| WO | 2015077327 A1 | 5/2015 | |
| WO | 2015185828 A1 | 12/2015 | |
| WO | 2018154225 A1 | 8/2018 | |

OTHER PUBLICATIONS

International Search Report dated May 17, 2022; International Application No. PCT/FR2022/050168; 3 pages (non-English).

Written Opinion dated May 17, 2022; International Application No. PCT/FR2022/050168; 5 pages (non-English).

Spanish Search Report and Written Opinion corresponding to Spanish Application No. 202390118; Issue Date, Nov. 8, 2023.

Cronier et al., "The concept of locking plates", Orthopaedics & Traumatology: Surgery & Research, 2010, 20 pages.

* cited by examiner

[Fig. 1]
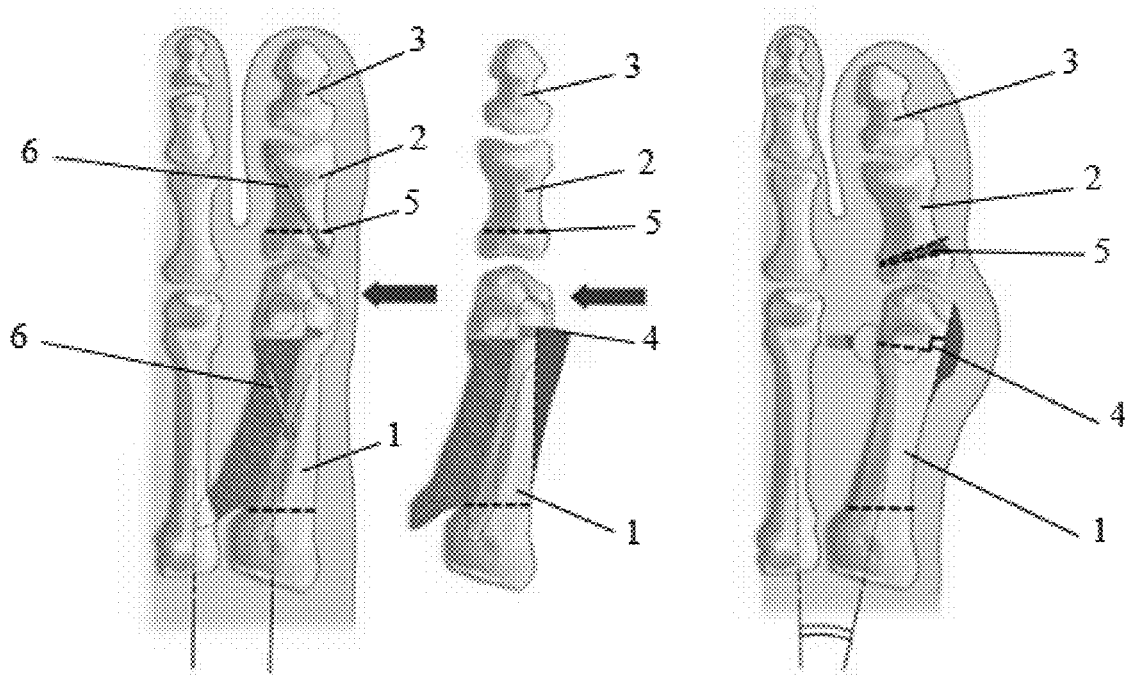
[Fig. 2]
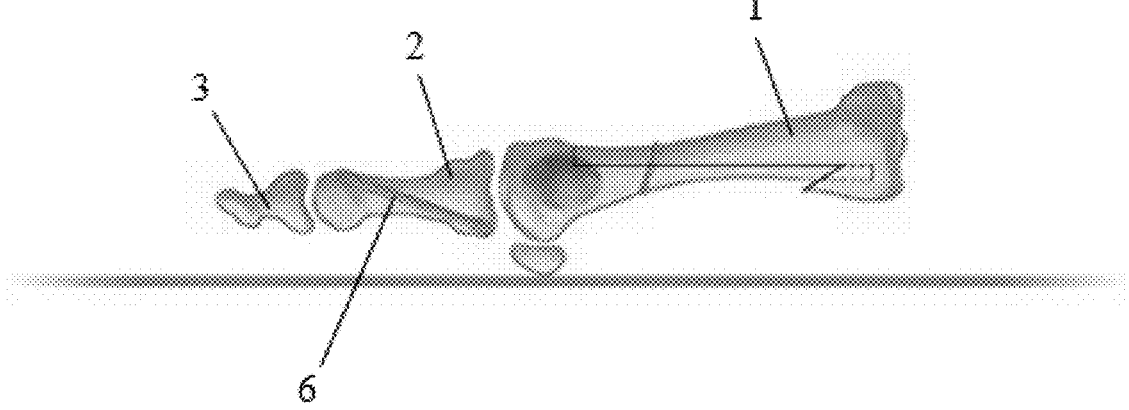

[Fig. 3]
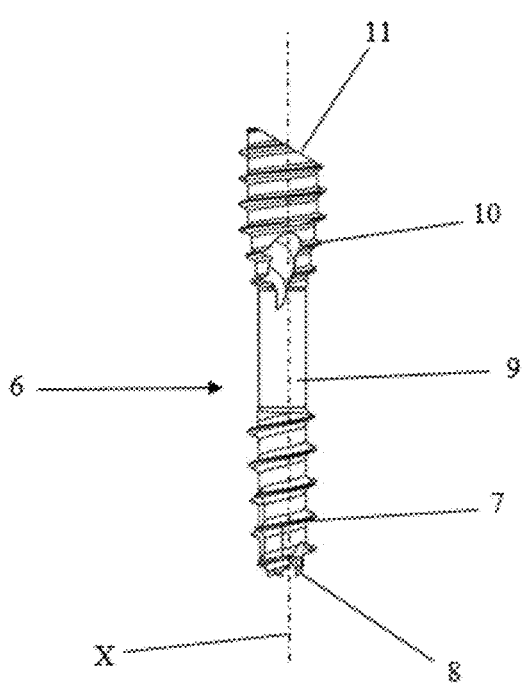
[Fig. 4]
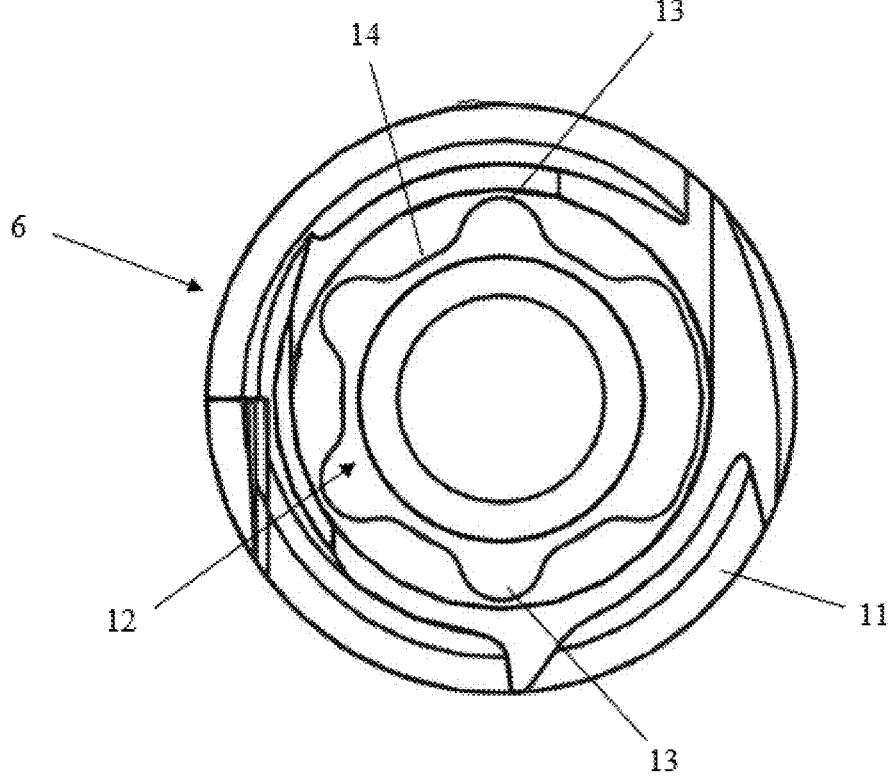

[Fig. 5]
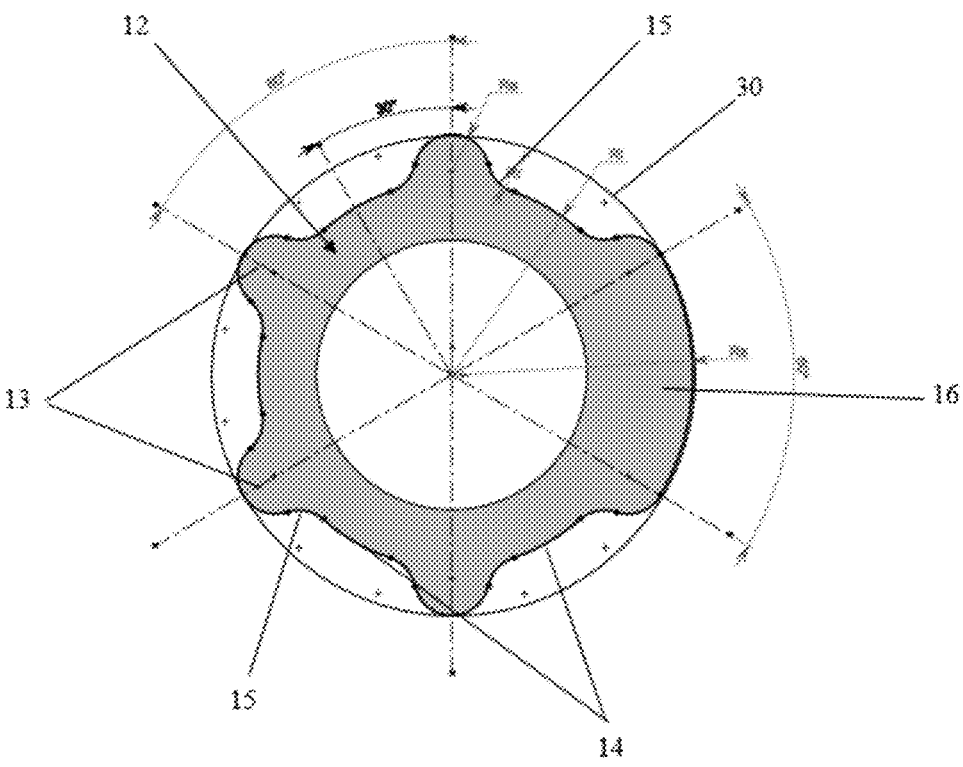
[Fig. 6]
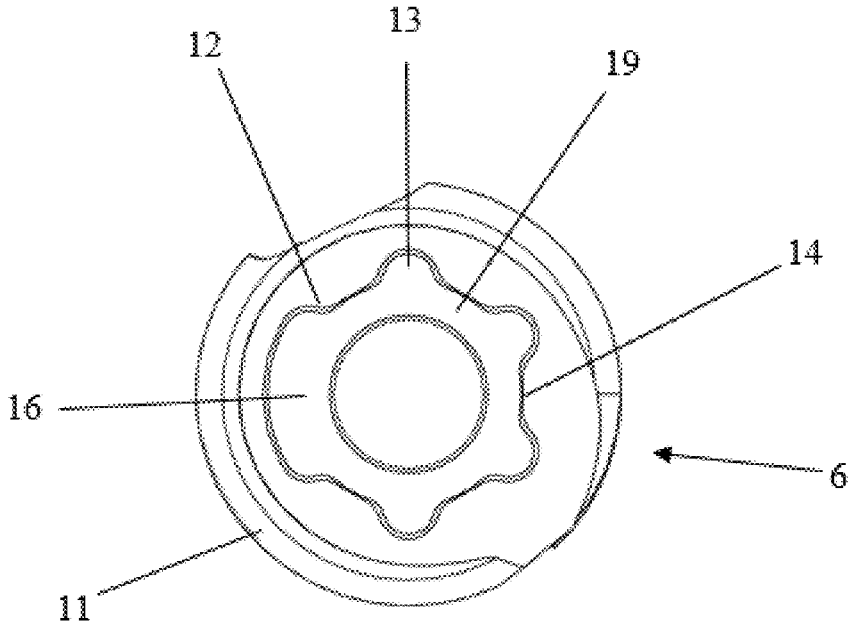

[Fig. 7]
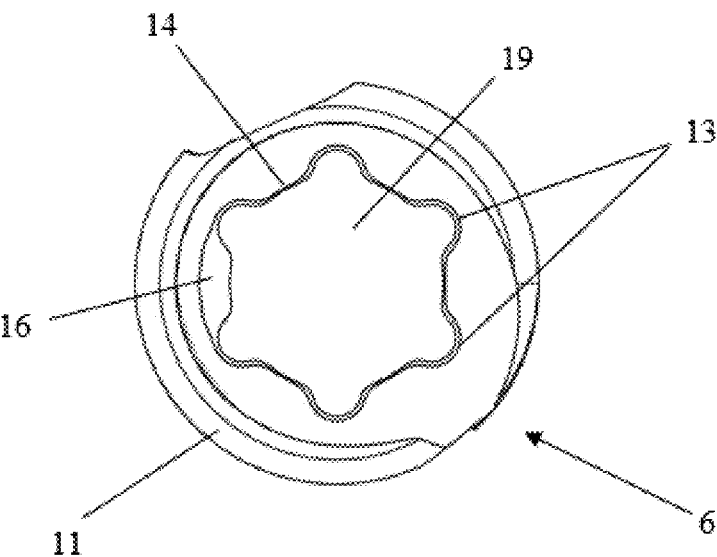
[Fig. 8]
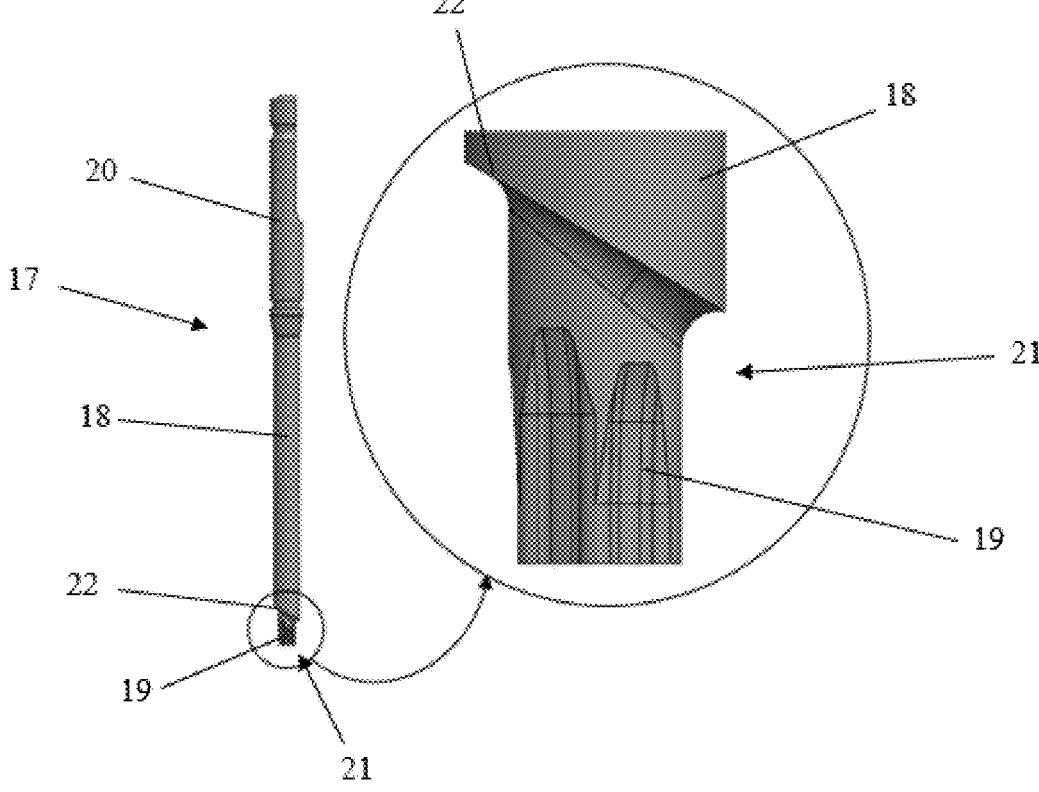

[Fig. 9]
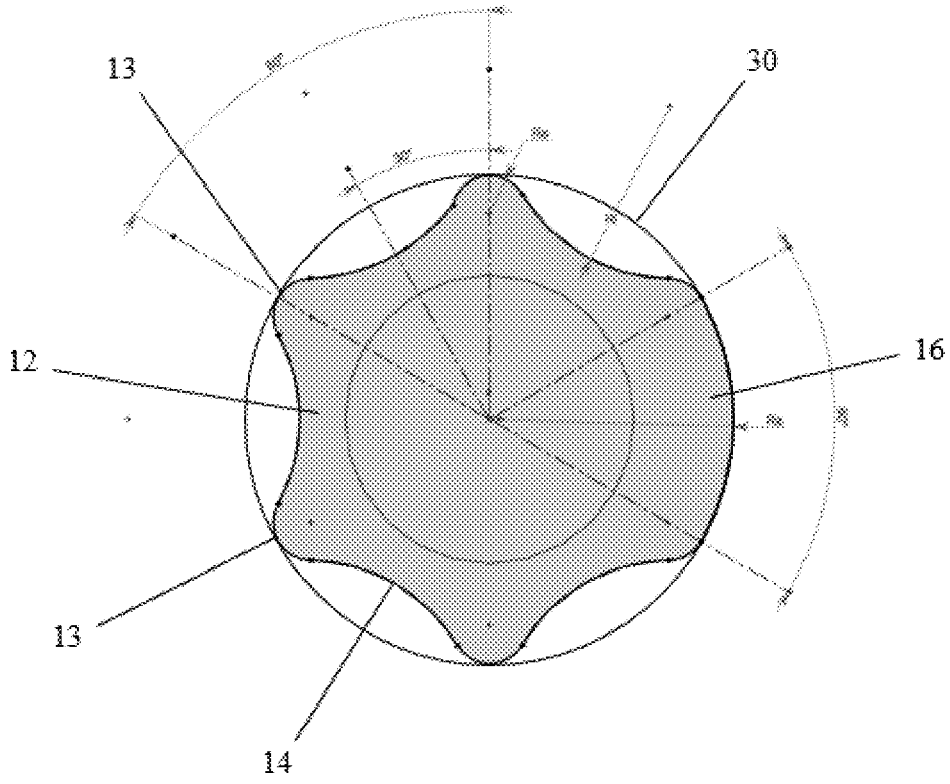
[Fig. 10]
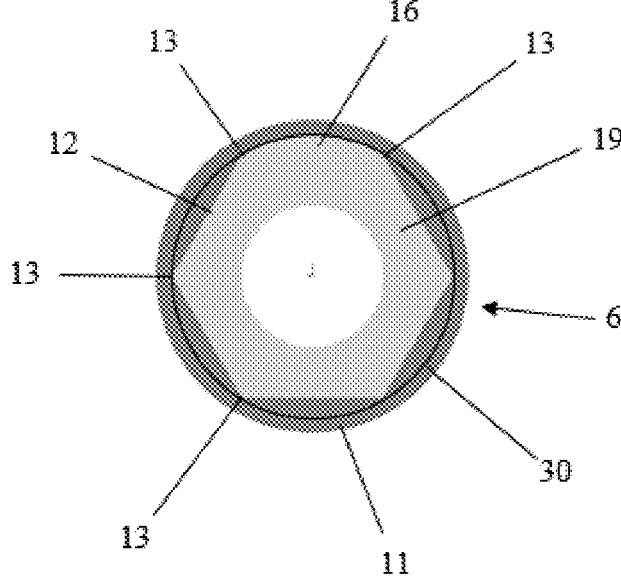

[Fig. 11]
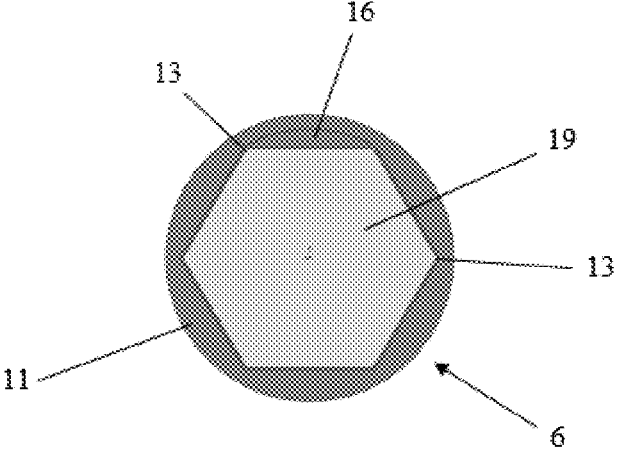
[Fig. 12]
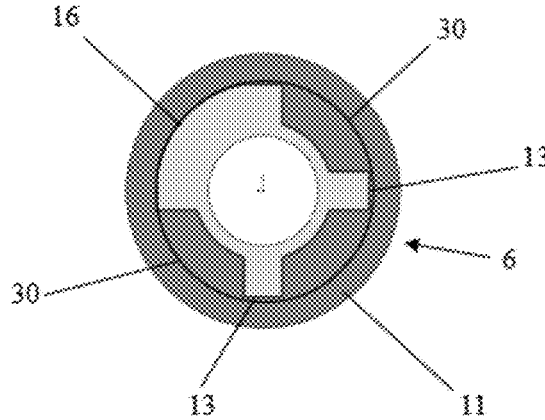

[Fig. 13]
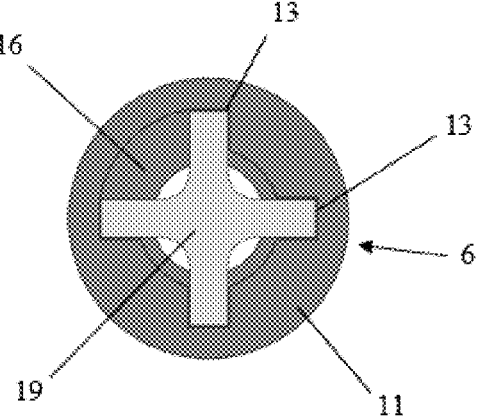

OSTEOSYNTHESIS SCREW WITH ANGULAR INDEXING RELATIVE TO THE SCREWDRIVER AND UNIVERSAL COMPATIBILITY

CROSS REFERENCE TO RELATED APPLICATIONS

This application is a National Stage of PCT Application No. PCT/FR2022/050168 filed on Jan. 31, 2022, which claims priority to French Patent Application No. 21/00926 filed on Feb. 1, 2021, the contents each of which are incorporated herein by reference thereto.

TECHNICAL FIELD

The present disclosure concerns a tightening screw intended to be actuated by a screwdriver, and a screwdriver adapted for this tightening screw. In particular, the present disclosure can be applied to the field of bone repair surgery, in particular for tightening and fastening an osteosynthesis screw in a bone fragment to be stabilized. More particularly, the present disclosure can be applied to the surgery of extremities of the limbs, such as feet, ankles, hands or wrists.

BACKGROUND

It is well known that osteosynthesis is a surgical operation which consists in fastening two bone portions together such as fragments of a cut or broken bone, or two bones close to each other, thanks to axial elements such as screws or pins made of metallic materials tolerated by the body, having a shape adapted to the elements to be treated.

In particular, osteosynthesis can be applied to chevron-type osteotomy operations, in a minimally invasive approach.

Hallux-valgus is a common deformity of the forefoot which results in an inward deviation called varus of the first metatarsal, and an outward deviation called valgus of the first phalanx. A type of surgical procedure making it possible to correct this deformity involves a chevron osteotomy, which is then fastened by one or several osteosynthesis screws in a minimally invasive approach.

The minimally invasive surgical approach consists in making small incisions in the skin and tissues to pass the instruments and implants required for the correction. The size of the scars is thus minimized, which offers a faster tissue rehabilitation compared to a conventional so-called open approach.

Such a surgical approach, with reference to FIGS. 1 and 2, usually includes several stages, the foot to be operated on including successively forwards for the big toe, a metatarsus 1, a proximal phalanx 2 and a distal phalanx 3, the inner side of the foot being that facing the axis of the body, and the metatarsus 1 having an abnormal inward inclination, and the proximal phalanx 2 having an abnormal outward inclination. The first stage of the surgical operation provides for a cut 4 of the metatarsus 1 in its front portion, formed at an angle, and a double cut 5 of the proximal phalanx 2 in its rear portion in order to remove a portion of the bone forming a corner. Then, the front portion of the metatarsus 1 is moved outwards relative to the rear portion, and the proximal phalanx 2 is moved inwards by having removed the portion of the bone forming the corner. An alignment along the axis of the foot, of the metatarsus 1 and of the proximal phalanx 2 thus modified is then substantially obtained. Finally, a first tightening screw 6 is inserted into both portions of the metatarsus 1 and a second screw 6 is inserted into both portions of the proximal phalanx 2, to fasten together each time these two portions. Each tightening screw 6 enters the inner side of the foot from the rear, after having made a minimum incision on the tissues arranged in the axis of the screw.

The screws used for osteosynthesis include a totally or partially threaded length, and a rear head comprising at the tip a driving recess intended to be actuated by a screwdriver. In particular, the heads may have a beveled rear end face, generally inclined at an angle comprised between 30° and 45° with respect to the main axis of the screw, which must be arranged in a particular orientation in order to conform to the external contour of the bone after the complete introduction of this screw inside, to limit the damage of the surrounding tissues. For minimally invasive surgical procedure with this type of screw, as the final phase of tightening the screw into the bone site approaches, tissues may visually conceal the beveled rear face of the screw.

Furthermore, there are different known types of driving recess for an osteosynthesis screw. A type of driving recess for an osteosynthesis screw is described in particular in the international patent application WO2015/185828.

The document WO2015/185828 describes a tightening member comprising six convex lobes and six concave lobes alternately distributed about a central axis so that each concave lobe connects two consecutive convex lobes about the central axis. In a first variant, the convex lobes comprise at least three cylindrical convex lobes and at least two separate conical convex lobes. In a second variant, the concave lobes comprise three cylindrical concave lobes and at least two separate conical concave lobes. The recess of the tightening member is capable of receiving a complementary male shape formed at the tip of a screwdriver. The generally cylindrical six-lobe shape of the screw or the screwdriver has, in addition, on some lobes a slightly conical portion allowing by an axial thrust a small tightening of the screwdriver in the recess, in order to ensure that the screw is temporarily held at the tip of the screwdriver. In this way, a loss of the connection between the screwdriver and the screw before or during assembly can be avoided.

In addition, for a screw having a beveled rear face, it is known to use a screwdriver having a visual mark indicating an orientation about its axis, which makes it possible, by fastening the screw on the screwdriver in a particular manner with respect to this mark, to constantly know at the end of screwing the position of this inclined rear face when it is no longer visible.

However, if the screwing is not completed while the rear face of the screw concealed by the tissues is no longer visible, in the event of uncoupling of the screwdriver on the recess of the screw, for example during a wrong move, the surgeon must perform a complementary operation to find the inclination of this rear face, such as unscrewing the screw, or taking an X-ray image visualizing this inclination. There is then a harmful waste of time during the patient's operation.

In order to overcome this drawback, a tightening screw has already been devised which allows a unique orientation of the screwdriver engaged on the recess of the screw. This is in particular the case of the international patent application WO2018/154225.

The document WO2018/154225 describes a tightening screw for osteosynthesis including a thread arranged along a main axis, and at its rear end a recess having about the main axis angularly distributed regular shapes, which are adapted to receive complementary shapes of a screwdriver, the rear face of the screw having an inclination with respect to a transverse plane of the screw. The recess of this screw includes at least one particular shape different from the other regular shapes. This recess makes it possible to index the male portion of the screwdriver relative to the complementary female portion of the recess, this indexing being preferentially carried out thanks to a specific shape of the recess, derived from a hexalobular.

Although this type of the prior art recess perfectly performs the indexing function, once the osteosynthesis has been carried out or in the event of clinical failure, it may prove necessary to remove the implant and therefore to have the dedicated screwdriver bit complementary to the screw in order to carry out this operation. However, the practitioner required to remove the osteosynthesis material may not have the appropriate instrument (instrument set not available in the healthcare center, no prior identification of the placed implant . . . ) or the patient may undergo the procedure in another center and with another practitioner than during the initial surgery.

For the removal of osteosynthesis material, each healthcare facility has a set of generic instruments including bits for screws with hexagonal, hexalobular, cross type recess . . . . The set does not contain any specific instruments, thus complicating the removal process.

In addition, the shape of the prior art recess can be reduced to a suppression of one lobe compared to the conventional hexalobular recess, which reduces the amount of material in the section, thus reducing the mechanical strength in torsion.

BRIEF SUMMARY

One of the aims of the present disclosure is therefore to overcome these drawbacks by proposing a tightening screw for osteosynthesis of simple and inexpensive design, allowing indexing of the male portion of the screwdriver relative to the complementary female portion of the recess while being compatible with standard instruments.

To this end, and according to the present disclosure, there is proposed a tightening screw for osteosynthesis including at least one thread along a main axis and, at its so-called apical end, a recess having about said main axis angularly distributed regular shapes, which are adapted to receive complementary shapes of a screwdriver engaging in said cavity, the apical face of the screw having an inclination with respect to a transverse plane of the screw; said screw being remarkable in that the recess of the screw includes at least three regular shapes whose vertices are inscribed in a circle called a circumscribed circle and at least two adjacent vertices of the recess are connected to form a convex lobe, so-called indexing convex lobe, whose radius of curvature is equal to the radius of the circumscribed circle.

It is well understood that, by making on the tip of the screwdriver shapes complementary to those of the screw, comprising a particular complementary shape, the tightening screw according to the present disclosure makes it possible to obtain a unique orientation of the screwdriver engaged on the recess of the screw. In the event of uncoupling of the screwdriver before the end of the tightening operation while the rear face of the screw is no longer visible, the surgeon gently rotates the screwdriver by exerting a slight pressure until it fits on the recess of this screw, thus making it possible to find the unique orientation imposed by the particular shape. The surgeon then completes his tightening by monitoring an orientation visual mark of the screwdriver, to know for certain the orientation of the inclined rear face of the screw. Furthermore, the recess of the tightening screw according to the present disclosure also makes it possible to use standard instruments, that is to say a screwdriver with a hexalobular head of the torx type (registered trademark) or with a hexagonal or cross head depending on the general shape of the recess.

The tightening screw may comprise a basal end and/or a smooth central portion.

According to a first embodiment, the recess has a so-called hexalobular shape comprising 6 convex lobes separated by 6 intermediate spaces, said convex lobes forming the regular shapes.

According to a second embodiment, the recess has a hexagonal shape, the six vertices of the hexagon forming the regular shapes.

According to a third embodiment, the recess has the shape of a cross, the four vertices of the cross forming the regular shapes.

Furthermore, the recess has a generally cylindrical shape arranged coaxially with the axis of the screw and comprising a slightly conical portion.

In addition, the thread extends from the basal end to the apical end of the screw.

Alternatively, the tightening screw comprises a first so-called basal thread which extends from the basal end of the screw to the smooth central portion of the screw and a second so-called apical thread which extends from the smooth central portion of the screw to the apical end of the screw.

Preferably, the second apical thread has a diameter greater than the diameter of the first basal thread.

Furthermore, the diameter of the screw decreases from its apical end to its basal end.

Another object of the present disclosure concerns a screwdriver for tightening screws according to the present disclosure including a handle secured to a blade and, at the distal end of the blade, a tip having shapes complementary to those of the recess.

Advantageously, the screwdriver has a visual angular mark.

Said visual angular mark consists of a shoulder between the distal end of the blade and the tip of the screwdriver.

BRIEF DESCRIPTION OF THE DRAWINGS

Other advantages and features will become more apparent from the following description of several variants, given as non-limiting examples, of the tightening screw for osteosynthesis according to the present disclosure, with reference to the appended drawings in which:

FIG. 1 is a schematic representation of the different stages of surgery to reduce hallux valgus of the big toe using the so-called "scarf" surgical technique, with the foot seen from above, FIG. 2 is a schematic side view of the foot after the surgical procedure, FIG. 3 is a side view of a tightening screw for osteosynthesis according to the present disclosure, FIG. 4 is a top view of the tightening screw for osteosynthesis according to the present disclosure showing its drive recess, FIG. 5 is a schematic representation seen from above of the drive recess of the tightening screw for osteosynthesis according to the present disclosure, FIG. 6 is a top view of the tightening screw for osteosynthesis according to the present disclosure showing its drive recess and receiving a screwdriver of complementary shape, FIG. 7 is a top view of the tightening screw for osteosynthesis according to the present disclosure showing its drive recess and receiving a standard torx type (registered trademark) instrument screwdriver, FIG. 8 is a side view of a screwdriver capable of cooperating with the tightening screw for osteosynthesis according to the present disclosure, FIG. 9 is a schematic top view of a variant of the recess of the tightening screw for osteosynthesis according to the present disclosure receiving a screwdriver of complementary shape, FIG. 10 is a schematic top view of a second variant of the recess of the tightening screw for osteosynthesis according to the present disclosure receiving a screwdriver of complementary shape, FIG. 11 is a schematic top view of the variant of the recess of the tightening screw for osteosynthesis according to the present disclosure shown in FIG. 10 receiving a screwdriver of standard hexagonal shape, FIG. 12 is a schematic top view of a third variant of the recess of the tightening screw for osteosynthesis according to the present disclosure receiving a screwdriver of complementary shape, FIG. 13 is a schematic top view of the variant of the recess of the tightening screw for osteosynthesis according to the present disclosure shown in FIG. 12 receiving a standard cross-head screwdriver.

DETAILED DESCRIPTION

In the following description of the present disclosure, the same reference numerals refer to the same elements. Furthermore, the various views are not necessarily plotted to scale.

With reference to FIG. 3, the tightening screw 6 according to the present disclosure comprises a first so-called basal thread 7 which extends from the basal end 8 of the screw 6 to the smooth central portion 9 of the screw and a second so-called apical thread 10 which extends from the smooth central portion 9 of the screw 6 to the apical end 11 of the screw 6. The second apical thread 10 has a diameter greater than the diameter of the first basal thread 8. Furthermore, the diameter of the screw 6 decreases from its apical end 11 to the smooth central portion 9, the basal end 8 having a self-tapping shape which ensures the formation of the thread in the bone portions.

The apical end 11 of the screw 6 is planar and has an inclination with respect to a transverse plane of the screw 6, forming a bevel which can be comprised between 30° and 45°. Said apical end 11 of the screw 6 includes an axially directed driving recess, which is centered on the axis of the screw X, intended to receive a complementary shape of a screwdriver in order to drive it in rotation, as will be detailed below.

It will be observed that the screw 6 is of the compression screw type and it is quite obvious that the screw 6 may comprise a thread which extends from the basal end 8 to the apical end 11 of the screw 6 without however departing from the scope of the present disclosure.

With reference to FIGS. 4 and 5, the apical end 11 of the screw 6 includes an axially directed driving recess 12, which is centered on the axis of the screw X. In this particular embodiment, said recess 12 has five external convex lobes

13 separated by five intermediate spaces 14 so that four of the five external convex lobes are spaced apart by 60° and have an identical radius Re and that each external convex lobe 13 is separated by an intermediate space 14 defined by a central convex lobe having a radius Ri, tangentially connected by two convex lobes having a radius Rr. This feature makes it possible to increase the amount of material of the recess section, thus increasing its mechanical strength in torsion. Furthermore, each intermediate convex lobe 14 is oriented at 30° with respect to the adjacent external convex lobe 13 and one of the five external convex lobes 13 has a radius Rs and alone covers an angular sector of 60°, hereinafter referred to as indexing lobe 16.

The radii Re and Ri may, in an indicative and non-limiting manner, be defined as those of the six-lobe recess for screws of the ISO 10664 standard. In addition, the radius Rs of the indexing lobe 16 will be defined so that it is the result of the merging of two external convex lobes 13.

With reference to FIGS. 6 and 7, the recess 12 of the screw 6 can receive either the tip of a screwdriver having a shape strictly complementary to the shape of the recess 12, as shown in FIG. 6 or the tip of a standard torx type (registered trademark) screwdriver as shown in FIG. 7.

FIG. 8 shows a screwdriver 17 including, at the front of a metallic cylindrical rod called a blade 18, a tip 19 constituting a cylinder centered on the axis, intended to fit with a minimum clearance in the recess 12 of the apical end 11 of the screw 6. In particular, the tip 19 includes a succession of five shapes constituting regular lobes, each extending at an angle of 60°. On the remaining 60° there is an indexing lobe. A unique positioning of the screw 6 on the screwdriver 17 is obtained, which is given by fitting the two circular portions to each other. For the initial assembly of the screw 6 on the screwdriver 17, or after the start of insertion if the surgeon disengages the screwdriver from the screw and then wants to put it back, the unique angular positioning is necessarily obtained. In particular the recess 12 of the screw 6 or the tip 19 of the screwdriver 17, may include on some lobes a slightly conical shape opening towards the rear for the screw or closing towards the front for the screwdriver, in order to ensure, after an axial thrust, that the screw is held on the screwdriver.

Furthermore, the screwdriver 17 includes a handle 20 and a visual angular mark 21 which consists of a shoulder 22 between the distal end of the blade 18 and the tip 19 of the screwdriver 17, said shoulder 22 forming a bevel inclined at an angle comprised between 30° and 45°, arranged parallel to the apical end 11 of the screw 6 when it is fastened on this screwdriver 17. In this way the surgeon visualizes directly by looking at the handle 20 the angular position of the apical end 11 of the screw 6.

According to a first variant of the tightening screw according to the present disclosure, with reference to FIG. 9, the recess 12 of the screw 6 has five external convex lobes 13 separated by five internal concave lobes 14 so that four of the five external convex lobes 13 are spaced apart by 60° and have an identical radius Re, that each external convex lobe 13 is separated by a concave lobe 14 having an identical radius Ri, that each intermediate concave lobe 14 is oriented at 30° with respect to the adjacent external convex lobe 13 and that one of the five external convex lobes 13, called the indexing lobe 16, has a radius Rs and alone covers an angular sector of 60°.

According to a second variant, with reference to FIG. 10, the recess 12 of the screw 6 has a hexagonal shape, the six vertices 13 of the hexagon forming so-called regular shapes whose vertices are inscribed in a circle called the circumscribed circle 30 and at least two adjacent vertices 13 of the recess being connected to form a convex lobe called the indexing lobe 16 and whose radius of curvature is equal to the radius of the circumscribed circle 30. In the same way, the recess 12 of the screw 6 can receive either the tip 19 of a screwdriver having a shape strictly complementary to the shape of the recess 12, as shown in FIG. or the tip 19 of a standard hexagonal head screwdriver as shown in FIG. 11.

According to a third variant, with reference to FIG. 12, the recess 12 of the screw 6 has the shape of a cross, the four vertices of the cross forming so-called regular shapes 13 whose vertices are inscribed in a circle called the circumscribed circle 30 and at least two adjacent vertices 13 of the recess 12 being connected to form a convex lobe called the indexing lobe 16 and whose radius of curvature is equal to the radius of the circumscribed circle 30. In the same way, the recess 12 of the screw 6 can receive either the tip 19 of a screwdriver having a shape strictly complementary to the shape of the recess 12, as shown in FIG. 12 or the tip 19 of a standard cross-head screwdriver as shown in FIG. 13.

Thus, it will be observed that, in general, the tightening screw 6 for osteosynthesis includes at least one thread 7, 10 along a main axis X and at its so-called apical end 11 a recess 12 having about said main axis 13 angularly distributed regular shapes, which are adapted to receive complementary shapes of a screwdriver 17 engaging in said recess 12, the apical face 11 of the screw having an inclination with respect to a transverse plane of the screw 6, and the recess of the screw includes at least three regular shapes 13 whose vertices are inscribed in a circle called the circumscribed circle 30 and at least two adjacent vertices 13 of the recess 12 are connected to form a convex lobe 16, so-called indexing convex lobe, whose radius of curvature is equal to the radius of the inscribed circle 30.

Finally, it is quite obvious that the examples just given are only particular illustrations and in no way limiting as to the fields of application of the present disclosure.

The invention claimed is:

1. A tightening screw for osteosynthesis including at least one thread along a main axis of the tightening screw and at an apical end of the tightening screw a recess having about the main axis angularly distributed regular shapes, which are adapted to receive complementary shapes of a screwdriver engaging in the recess, wherein the recess of the tightening screw includes at least three regular shapes whose vertices are inscribed in a circumscribed circle and at least two adjacent vertices of the recess are connected to form an indexing lobe, the indexing lobe having a radius of curvature that is equal to a radius of the circumscribed circle, wherein the recess has a hexalobular shape comprising 6 convex lobes separated by 6 intermediate spaces, the convex lobes forming the at least three regular shapes.

2. The tightening screw according to claim 1, wherein the recess includes a generally cylindrical shape arranged coaxially to the main axis of the tightening screw and comprising a slightly conical portion.

3. The tightening screw according to claim 1, wherein the at least one thread extends from a basal end to the apical end of the tightening screw.

4. The tightening screw according to claim 1, wherein the tightening screw comprises a first basal thread which extends from a basal end of the tightening screw to a smooth central portion of the tightening screw and a second apical thread which extends from the smooth central portion of the tightening screw to the apical end of the screw.

5. The tightening screw according to claim 4, wherein the second apical thread has a diameter greater than a diameter of the first basal thread.

6. The tightening screw according to claim 4, wherein a diameter of the tightening screw decreases from its apical end to its smooth central portion.

7. The tightening screw according to claim 1 wherein an apical face of the tightening screw has an inclination with respect to a transverse plane of the tightening screw.

8. The tightening screw according to claim 1, wherein each intermediate space is defined by a central convex lobe.

9. A screwdriver for tightening screws for osteosynthesis, each tightening screw of the tightening screws including at least one thread along a main axis and at an apical end of each tightening screw of the tightening screws a recess having about the main axis angularly distributed regular shapes, which are adapted to receive complementary shapes of the screwdriver engaging in the recess, wherein the recess has a hexalobular shape comprising 6 convex lobes separated by 6 intermediate spaces, the convex lobes having vertices which are inscribed in a circumscribed circle and at least two adjacent vertices of the recess are connected to form an indexing lobe, the indexing lobe having a radius of curvature that is equal to a radius of the circumscribed circle, the screwdriver including a handle secured to a blade and, at a distal end of the blade, a tip having shapes complementary to those of the recess.

* * * * *